US009498487B2

(12) United States Patent
Liu et al.

(10) Patent No.: US 9,498,487 B2
(45) Date of Patent: Nov. 22, 2016

(54) TOPICAL CROMOLYN FORMULATIONS

(75) Inventors: Puchun Liu, Tarrytown, NY (US);
Steven Dinh, Briarcliff Manor, NY (US); Ehud Arbit, Englewood, NJ (US); Michael M. Goldberg, Tarrytown, NY (US)

(73) Assignee: EMISPHERE TECHNOLOGIES, INC., Roseland, NJ (US)

( * ) Notice: Subject to any disclaimer, the term of this patent is extended or adjusted under 35 U.S.C. 154(b) by 1419 days.

(21) Appl. No.: 11/569,285

(22) PCT Filed: May 19, 2005

(86) PCT No.: PCT/US2005/017816
§ 371 (c)(1),
(2), (4) Date: Jan. 30, 2009

(87) PCT Pub. No.: WO2005/112943
PCT Pub. Date: Dec. 1, 2005

(65) Prior Publication Data
US 2009/0209635 A1 Aug. 20, 2009

Related U.S. Application Data

(60) Provisional application No. 60/572,896, filed on May 19, 2004.

(51) Int. Cl.
*A61K 31/352* (2006.01)
*A61K 31/609* (2006.01)
*A61K 9/00* (2006.01)
*A61K 9/06* (2006.01)
*A61K 47/10* (2006.01)
*A61K 47/18* (2006.01)

(52) U.S. Cl.
CPC .......... *A61K 31/609* (2013.01); *A61K 9/0014* (2013.01); *A61K 9/06* (2013.01); *A61K 47/10* (2013.01); *A61K 47/183* (2013.01)

(58) Field of Classification Search
CPC .. A61K 31/609; A61K 47/10; A61K 47/183; A61K 9/0014; A61K 9/06; F16K 31/44; G05D 7/0106
USPC ........................... 514/465, 12, 784; 424/85.2
See application file for complete search history.

(56) References Cited

U.S. PATENT DOCUMENTS

| | | | | |
|---|---|---|---|---|
| 5,576,346 | A | * | 11/1996 | Clemente et al. ............ 514/456 |
| 5,650,386 | A | | 7/1997 | Leone-Bay et al. |
| 5,773,647 | A | | 6/1998 | Leone-Bay et al. |
| 5,866,536 | A | | 2/1999 | Leone-Bay et al. |
| 6,225,356 | B1 | * | 5/2001 | Jones, III ................. 514/772.3 |
| 6,420,418 | B1 | * | 7/2002 | Hagmann et al. ............ 514/471 |

FOREIGN PATENT DOCUMENTS

| | | |
|---|---|---|
| GB | 2337461 B | 10/2003 |
| WO | WO 94/23767 | 10/1994 |
| WO | WO 95/28838 | 11/1995 |
| WO | WO 95/28920 | 11/1995 |
| WO | WO 96/09813 | 4/1996 |
| WO | WO 96/10396 | 4/1996 |
| WO | WO 96/12473 | 5/1996 |
| WO | WO 96/12475 | 5/1996 |
| WO | WO 96/30036 | 10/1996 |
| WO | WO 96/33699 | 10/1996 |
| WO | WO 97/31938 | 9/1997 |
| WO | WO 97/36480 | 10/1997 |
| WO | WO 98/21951 | 5/1998 |
| WO | WO 98/25589 | 6/1998 |
| WO | WO 98/34632 | 8/1998 |
| WO | WO 98/49135 | 11/1998 |
| WO | WO 99/16427 | 4/1999 |
| WO | WO 00/06534 | 2/2000 |
| WO | WO 00/07979 | 2/2000 |
| WO | WO 00/11690 | 3/2000 |
| WO | WO 00/40203 * | 7/2000 |
| WO | WO 00/46182 | 8/2000 |
| WO | WO 00/47188 | 8/2000 |
| WO | WO 00/48589 | 8/2000 |
| WO | WO 00/50386 | 8/2000 |
| WO | WO 00/59480 | 10/2000 |
| WO | WO 00/59863 | 10/2000 |
| WO | WO 01/32130 | 5/2001 |
| WO | WO 01/32596 | 5/2001 |
| WO | WO 01/34114 | 5/2001 |
| WO | WO 01/44199 | 6/2001 |
| WO | WO 01/51454 | 7/2001 |
| WO | WO 01/70219 | 9/2001 |
| WO | WO 01/92206 | 12/2001 |
| WO | WO 02/02509 | 1/2002 |
| WO | WO 02/15959 | 2/2002 |
| WO | WO 02/16309 | 2/2002 |
| WO | WO 02/19969 | 3/2002 |
| WO | WO 02/20466 | 3/2002 |
| WO | WO 02/070438 | 9/2002 |
| WO | WO 02/100338 | 12/2002 |
| WO | WO 03/026582 * | 4/2003 |
| WO | WO 03/045306 | 6/2003 |
| WO | WO-03045331 A2 | 6/2003 |
| WO | WO 03/057170 | 7/2003 |
| WO | WO 03/057650 | 7/2003 |

OTHER PUBLICATIONS

Transdermal. http://medical-dictionary.thefreedictionary.com/transdermal. Miller-Keane Encyclopedia and Dictionary of Medicine, Nursing, and Allied Health, Seventh Edition. © 2003.*
The Hand Book of Preservatives (Isopropyl myristate p. 427 2004).*
Database WPI, Week 200009, Thomas Scientific, London, GB; AN 2000-101030, XP002684026 (Abstract of JP11335281).
Supplementary European Search Report issued in EP05752032 on Sep. 25, 2012.

* cited by examiner

*Primary Examiner* — Anna Falkowitz
(74) *Attorney, Agent, or Firm* — Blank Rome LLP

(57) ABSTRACT

The present invention provides a topical composition comprising (a) at least one delivery agent compound and (b) a cromoglycic acid compound. Methods of treatment, and methods of preparing the topical composition are also provided.

12 Claims, 10 Drawing Sheets

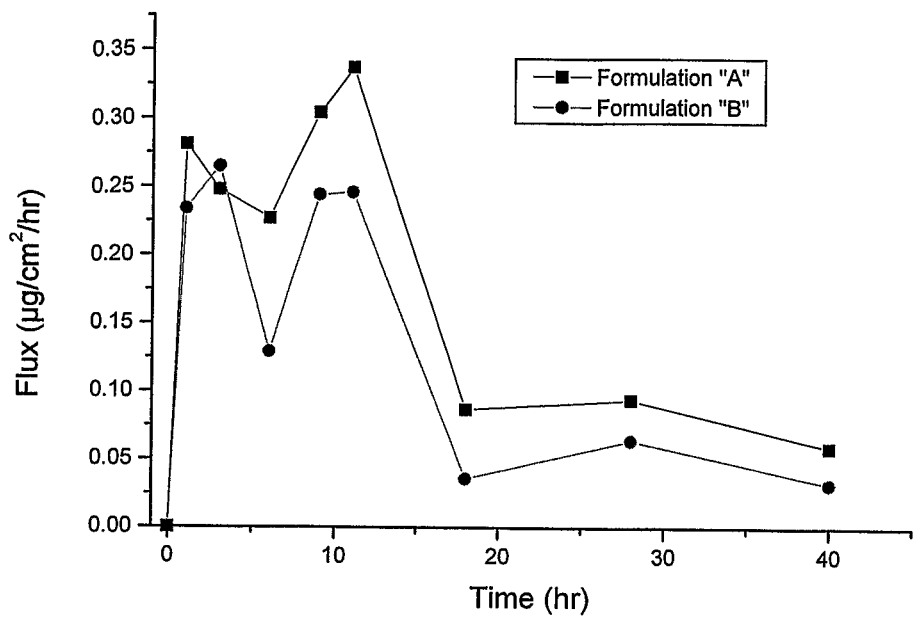
Figure 1: Percutaneous Absorption of $^3$H-Cromoglycate: Flux Results
(Mean from 1 Donor as μg/cm$^2$/hr)

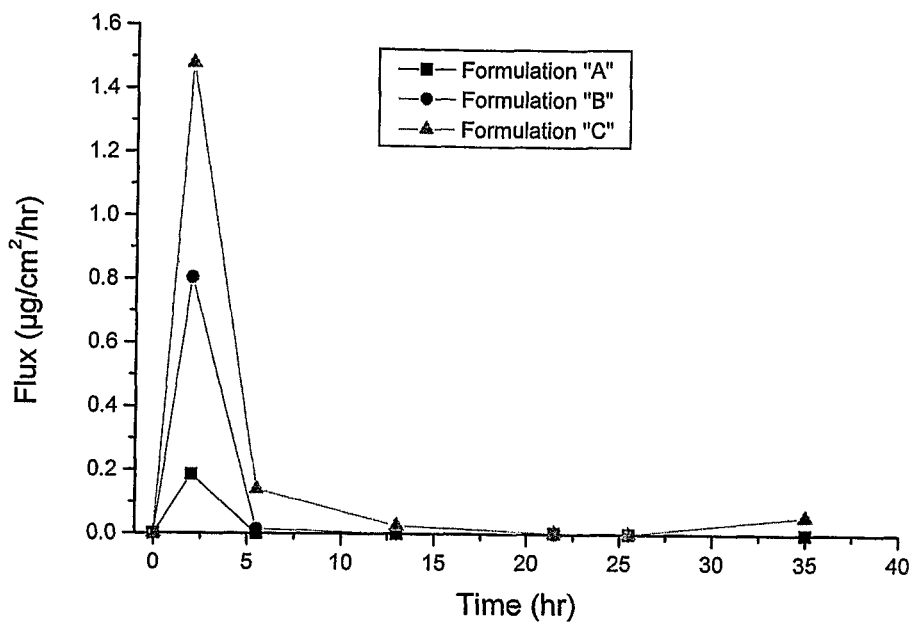
Figure 2: Percutaneous Absorption of $^3$H-Cromoglycate: Flux Results
(Mean from 1 Donor as µg/cm$^2$/hr)

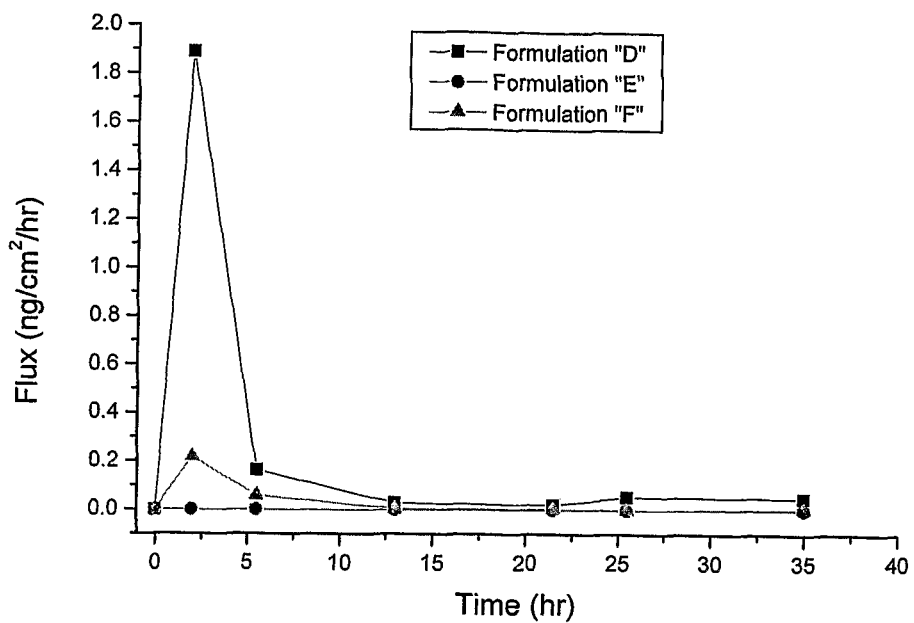
Figure 3: Percutaneous Absorption of $^3$H-Cromoglycate: Flux Results
(Mean from 1 Donor as ng/cm$^2$/hr)

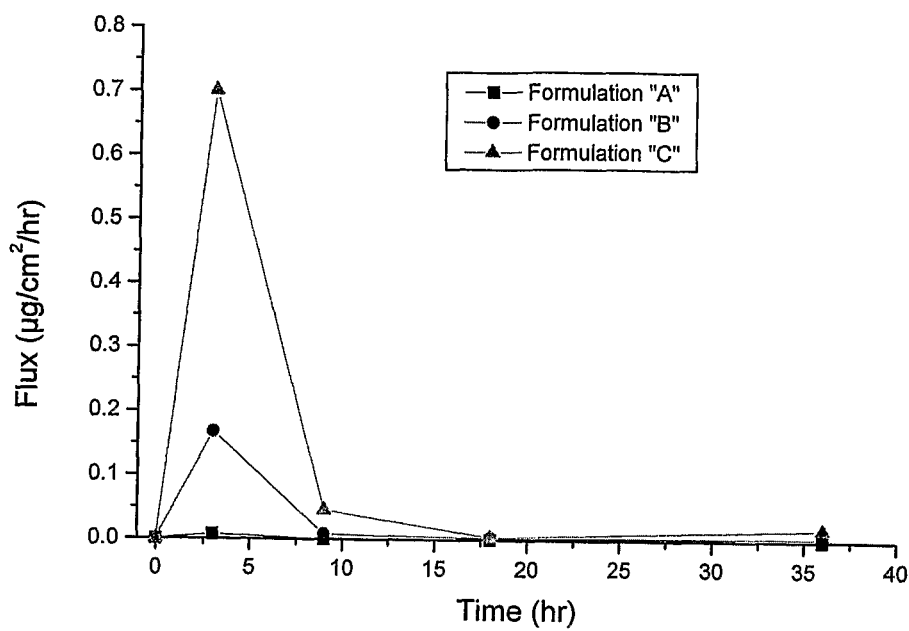
Figure 4: Percutaneous Absorption of $^3$H-Cromoglycate: Flux Results
(Mean from 1 Donor as µg/cm$^2$/hr)

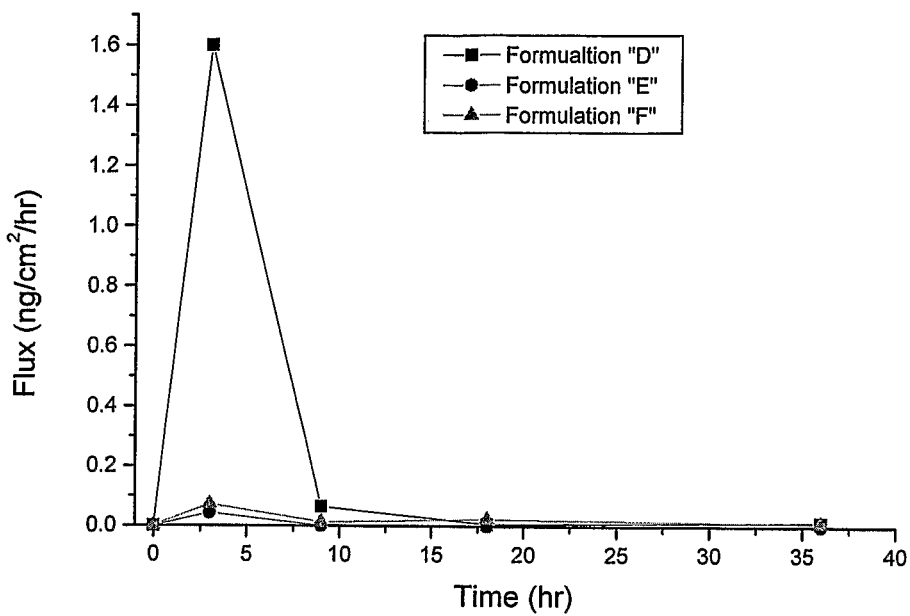
Figure 5: Percutaneous Absorption of $^3$H-Cromoglycate:
Flux Results
(Mean from 1 Donor as ng/cm$^2$/hr)

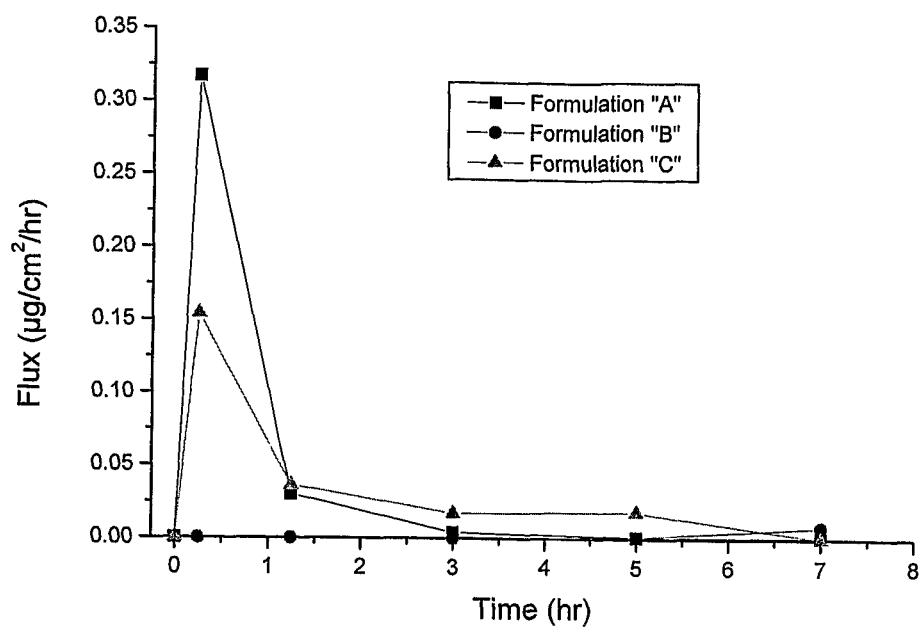
Figure 6: Percutaneous Absorption of $^3$H-Cromoglycate:
Flux Results
(Mean from 2 - 3 Donor as µg/cm$^2$/hr)

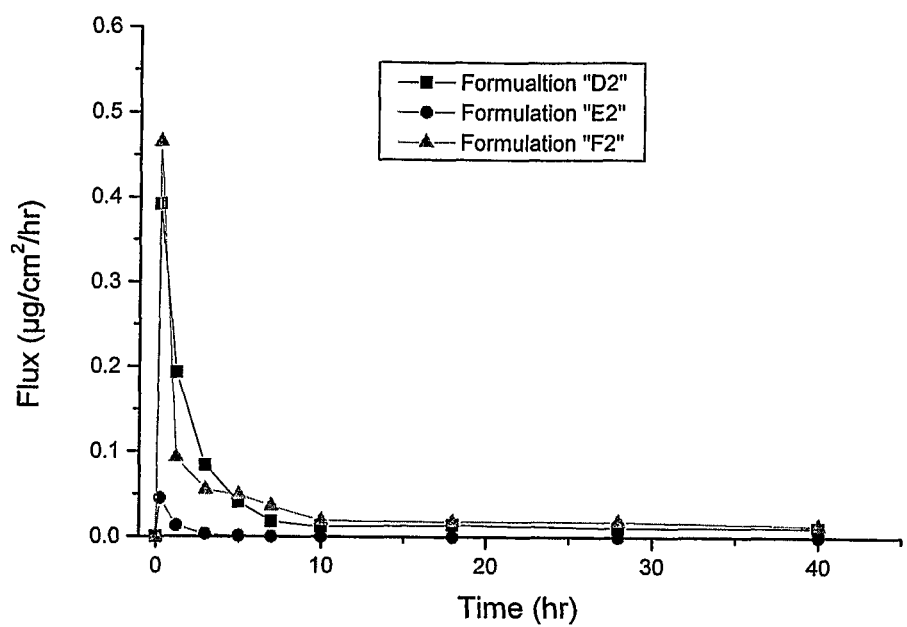
Figure 7: Percutaneous Absorption of $^3$H-Cromoglycate: Flux Results
(Mean from 3 Donors as ng/cm$^2$/hr)

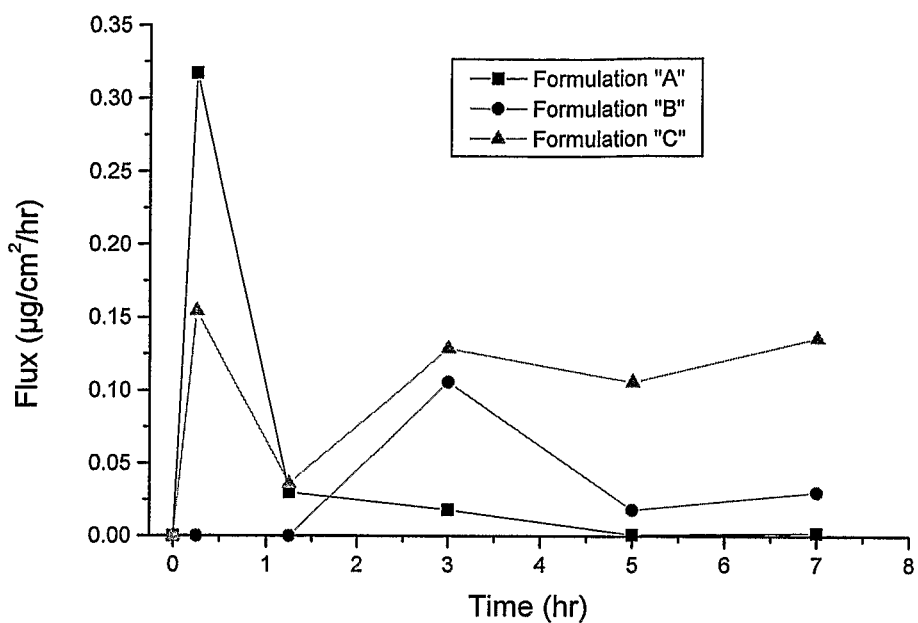
Figure 8: Percutaneous Absorption of $^3$H-Cromoglycate: Overall Study Summary Flux Results
(Mean from 4-5 Donors as µg/cm$^2$/hr)

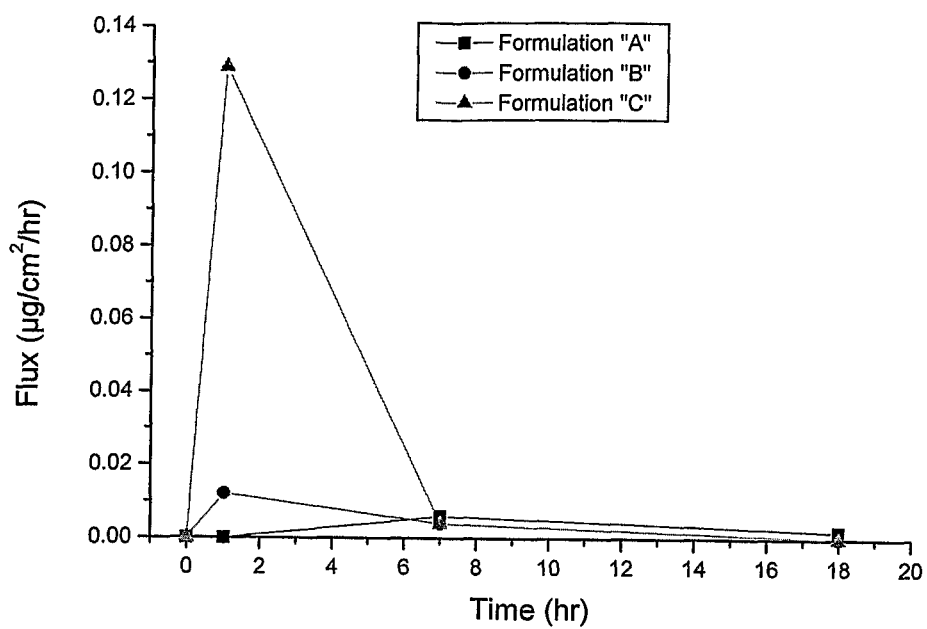
Figure 9: Percutaneous Absorption of $^3$H-Cromoglycate:
Analysis by HPLC: Summary Flux Results
($\mu g/cm^2/hr$)

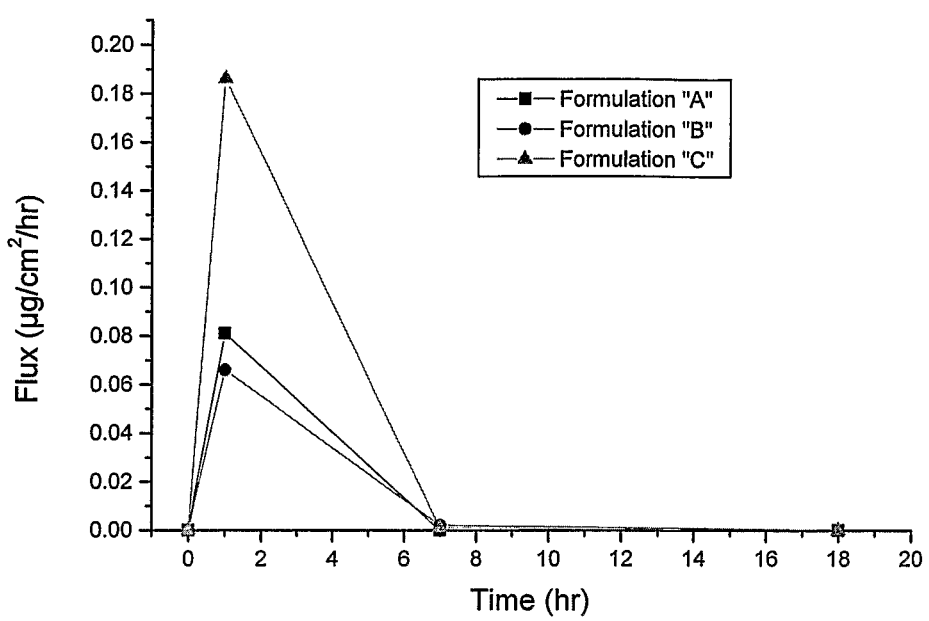
Figure 10: Percutaneous Absorption of $^3$H-Cromoglycate:
Analysis by Liquid Scintillation Counting
Summary Flux Results
($\mu g/cm^2/hr$)

TOPICAL CROMOLYN FORMULATIONS

This application claims the benefit of U.S. Provisional Application No. 60/572,896, filed May 19, 2004. This application is hereby incorporated by reference in its entirety.

FIELD OF THE INVENTION

The present invention relates to topical formulations containing cromolyn or a last or analog thereof, such as cromolyn sodium.

BACKGROUND OF THE INVENTION

Skin conditions, such as atopic dermatitis, are a widespread medical problem, with an increasing rate of prevalence. It has been reported that topically administered sodium cromolyn, which is the disodium salt of cromoglycic acid, can be included in an effective protocol for the treatment of such skin conditions. See. e.g., Kimata et al. "Effect of topical cromoglycate solution on atopic dermatitis: combined treatment of sodium cromoglycate solution with the oral anti-allergic medication, oxatomide", Eur. J. Pediatr. 153:66-71 (1994).

There is a need for a composition which provides higher epidermal layer concentrations of cromolyn and would therefore increase its therapeutic benefits in the treatment of skin conditions.

SUMMARY OF THE INVENTION

The present invention is a topical composition comprising (a) at least one delivery agent compound and (b) a cromolyn component selected from cromolyn (i.e. cromoglycic acid) pharmaceutically acceptable salts thereof, pharmaceutically acceptable analogs thereof, and any combination of any of the foregoing. Suitable salts of cromolyn include, but are not limited to, disodium cromoglycate (cromolyn sodium). In one embodiment of the invention, the composition includes an effective amount of the cromolyn component and a delivery agent compound to treat or prevent the onset of a skin condition.

The delivery agent compound improves the retention of the cromolyn component in the epidermis. For instance, the topical composition including a delivery agent compound can yield higher epidermis-layer concentrations of the cromolyn component over eight and 48 hours after a single administration than a similar topical composition without the delivery agent compound.

In one embodiment of the present invention, the delivery agent compound has the following structure, or a pharmaceutically acceptable salt thereof:

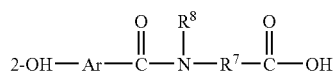

Formula A wherein
Ar is phenyl or naphthyl;
Ar is optionally substituted with one or more of —OH, halogen, $C_1$-$C_4$ alkyl, $C_1$-$C_4$ alkenyl, $C_1$-$C_4$ alkoxy or $C_1$-$C_4$ haloalkoxy;
$R^7$ is $C_4$-$C_{20}$ alkyl, $C_4$-$C_{20}$ alkenyl, phenyl, naphthyl, ($C_1$-$C_{10}$ alkyl)phenyl, ($C_1$-$C_{10}$ alkenyl)phenyl, ($C_1$-$C_{10}$ alkyl)naphthyl, ($C_1$-$C_{10}$ alkenyl)naphthyl, phenyl($C_1$-$C_{10}$ alkyl), phenyl($C_1$-$C_{10}$ alkenyl), naphthyl($C_1$-$C_{10}$ alkyl), or naphthyl ($C_1$-$C_{10}$ alkenyl);
$R^8$ is hydrogen, $C_1$ to $C_4$ alkyl, $C_2$ to $C_4$ alkenyl, $C_1$ to $C_4$ alkoxy, or $C_1$-$C_4$ haloalkoxy;
$R^7$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, —$CO_2R^9$, or any combination thereof;
$R^9$ is hydrogen, $C_1$ to $C_4$ alkyl, or $C_2$ to $C_4$ alkenyl; and
$R^7$ is optionally interrupted by oxygen, nitrogen, sulfur or any combination thereof.

In one embodiment, the delivery agent compounds are not substituted with an amino group in the position alpha to the acid group.

Suitable delivery agent compounds include, but are not limited to, N-(8-[2-hydroxybenzoyl]-amino)caprylic acid and salts thereof, e.g., a sodium salt of N-(8-[2-hydroxybenzoyl]-amino)caprylic acid, such as a mono- or di-sodium salt, N-(8-[2-hydroxybenzoyl]-amino)decanoic acid and pharmaceutically acceptable salts thereof, including its monosodium salt, 4-[(4-chloro-2-hydroxy-benzoyl)amino]butanoic acid (also known as 4-[(2-hydroxy-4-chlorobenzoyl)amino]butanoate) and pharmaceutically acceptable salts thereof, including its sodium salt (e.g., monosodium salt), N-(8-[2-hydroxy-5-chlorobenzoyl]-amino)octanoic acid (also known as 8-(N-2-hydroxy-5-chlorobenzoyl)aminocaprylic acid)) and pharmaceutically acceptable salts thereof, including its monosodium salt, and 8-(N-2-hydroxy-4-methoxybenzoyl)-aminocaprylic acid and pharmaceutically acceptable salts thereof, including its monosodium salt.

According to one embodiment, $R^7$ in Formula A is selected from $C_8$-$C_{20}$ alkyl, $C_8$-$C_{20}$ alkenyl, phenyl, naphthyl, ($C_1$-$C_{10}$ alkyl)phenyl, ($C_1$-$C_{10}$ alkenyl)phenyl, ($C_1$-$C_{10}$ alkyl) naphthyl, ($C_1$-$C_{10}$ alkenyl)naphthyl, phenyl($C_1$-$C_{10}$ alkyl), phenyl($C_1$-$C_{10}$ alkenyl), naphthyl($C_1$-$C_{10}$ alkyl), and naphthyl($C_1$-$C_{10}$ alkenyl).

According to another embodiment, $R^7$ in Formula A is selected from $C_8$-$C_{20}$ alkyl, and $C_8$-$C_{20}$ alkenyl.

In another embodiment of the present invention, the delivery agent compound has the following structure, or a pharmaceutically acceptable salt thereof:

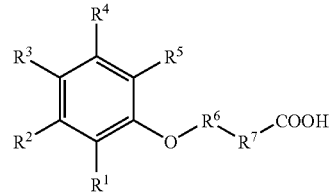

Formula B wherein
$R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)$R^8$, —$NO_2$, —$NR^9R^{10}$, or —$N^+R^9R^{10}R^{11}$ ($R^{12}$)$^-$;
$R^5$ is H, —OH, —$NO_2$, halogen, —$CF_3$, —$NR^{14}R^{15}$, —$N^+R^{14}R^{15}R^{16}$ ($R^{13}$)$^-$, amide, $C_1$-$C_{12}$ alkoxy, $C_1$-$C_{12}$ alkyl, $C_2$-$C_{12}$ alkenyl, carbamate, carbonate, urea, or —C(O)$R^{18}$;
$R^5$ is optionally substituted with halogen, —OH, —SH, or —COOH;
$R^5$ is optionally interrupted by O, N, S, or —C(O)—;
$R^6$ is a $C_1$-$C_{12}$ alkylene, $C_2$-$C_{12}$ alkenylene, or arylene;

$R^6$ is optionally substituted with a $C_1$-$C_4$ alkyl, $C_2$-$C_4$ alkenyl, $C_1$-$C_4$ alkoxy, —OH, —SH, halogen, —$NH_2$, or —$CO_2R^8$;

$R^6$ is optionally interrupted by O or N;

$R^7$ is a bond or arylene;

$R^7$ is optionally substituted with —OH, halogen, —C(O)$CH_3$, —$NR^{10}R^{11}$, or —$N^+R^{10}R^{11}R^{12}$ $(R^{13})^-$;

each occurrence of $R^8$ is independently H, $C_1$-$C_4$ alkyl, $C_2$-$C_4$ alkenyl, or —$NH_2$;

$R^9$, $R^{10}$, $R^{11}$, and $R^{12}$ independently H or $C_1$-$C_{10}$ alkyl;

$R^{13}$ is a halide, hydroxide, sulfate, tetrafluoroborate, or phosphate;

$R^{14}$, $R^{15}$ and $R^{16}$ are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, or —C(O)$R^{17}$;

$R^{17}$ is —OH, $C_1$-$C_{10}$ alkyl, or $C_2$-$C_{12}$ alkenyl; and $R^{18}$ is H, $C_1$-$C_6$ alkyl, —OH, —$NR^{14}R^{15}$, or $N^+R^{14}R^{15}R^{16}(R^{13})$—.

In one particular embodiment, when $R^1$, $R^2$, $R^3$, $R^4$, and $R^5$ are H, and $R^7$ is a bond then $R^6$ is not a $C_1$-$C_6$, $C_9$ or $C_{10}$ alkyl.

In another embodiment, when $R^1$, $R^2$, $R^3$, and $R^4$ are H, $R^5$ is —OH, and $R^7$ is a bond then $R^6$ is not a $C_1$-$C_3$ alkyl.

In yet another embodiment, when at least one of $R^1$, $R^2$, $R^3$, and $R^4$ is not H, $R^5$ is —OH, and $R^7$ is a bond, then $R^6$ is not a $C_1$-$C_4$ alkyl.

In yet another embodiment, when $R^1$, $R^2$, and $R^3$ are H, $R^4$ is —$OCH_3$, $R^5$ is —C(O)$CH_3$, and $R^6$ is a bond then $R^7$ is not a $C_3$ alkyl.

In yet another embodiment, when $R^1$, $R^2$, $R^4$, and $R^5$ are H, $R^3$ is —OH, and $R^7$ is a bond then $R^6$ is not a methyl.

In yet another embodiment, $R^6$ of Formula B is a $C_8$-$C_{12}$ alkylene, $C_8$-$C_{12}$ alkenylene, or arylene.

In yet another embodiment of the present invention, the delivery agent compound has the following structure or a pharmaceutically acceptable salt thereof:

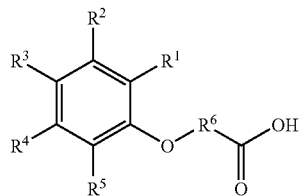

Formula C wherein $R^1$, $R^2$, $R^3$, $R^4$ and $R^5$ are independently H, —CN, —OH, —$OCH_3$, or halogen, at least one of $R^1$, $R^2$, $R^3$, $R^4$ and $R^5$ being —CN; and $R^6$ is a $C_1$-$C_{12}$ linear or branched alkylene, a $C_1$-$C_{12}$ linear or branched alkenylene, a $C_1$-$C_{12}$ linear or branched arylene, an alkyl(arylene) or an aryl(alkylene).

According to one embodiment, when $R^1$ is —CN, $R^4$ is H or —CN, and $R^2$, $R^3$, and $R^5$ are H, then $R^6$ is not methylene $((CH_2)_1)$.

In another embodiment, $R^6$ of Formula C is a $C_8$-$C_{12}$ linear or branched alkylene, a $C_8$-$C_{12}$ linear or branched alkenylene, an arylene, an alkyl(arylene) or an aryl(alkylene).

In yet another embodiment, $R^6$ of Formula C is a $C_8$-$C_{12}$ linear or branched alkylene, a $C_8$-$C_{12}$ linear or branched alkenylene Other suitable delivery agent compounds are disclosed in U.S. Pat. No. 6,627,228, which is hereby incorporated by reference.

In embodiments of the present invention, delivery agent compounds to be used in the topical composition along with the cromolyn component include, but are not limited to, a polymeric delivery agent comprising a polymer conjugated to a modified amino acid or derivative thereof via a linkage group selected from the group consisting of —NHC(O)NH—, —C(O)NH—, —NHC(O)—, —OOC—, —COO—, —NHC(O)O—, —OC(O)NH—, —$CH_2$NH—, —NH$CH_2$—, —$CH_2$NHC(O)O—, —OC(O)NH$CH_2$—, —$CH_2$NHCOCH$_2$O—, —OCH$_2$C(O)NHCH$_2$—, —NHC(O)CH$_2$O—, —OCH$_2$C(O)NH—, —NH—, —O—, and carbon-carbon bond. In one embodiment, the polymeric delivery agent is not a polypeptide or polyamino acid. In another embodiment, the modified amino acid has the structure of formula A, B, or C. In one embodiment, the polymeric delivery agent includes a modified amino acid having the structure:

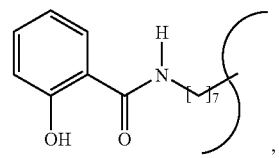

Formula D which is conjugated via a —COO group to a polymer having monomers derived from polyethylene glycol.

In one embodiment, the polymeric delivery agent is a modified amino acid having the structure of Formula D conjugated via a —COO group to a polymer having the structure:

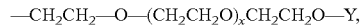

wherein x is from 1-14; and

Y is H or $CH_3$.

According to one embodiment, the polymeric delivery agent is compound having the structure of Formula D conjugated via a —COO group to a polymer having the structure:

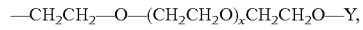

wherein x is 1-5; and

Y is $CH_3$ or H. For example, the polymeric delivery agent can be 8-(2-hydroxybenzoylamino)-octanoic acid 2-{2-[2-(2-{2-[2-(2-methoxyethoxy)ethoxy]ethoxy}-ethoxy)ethoxy]ethoxy}ethyl ester.

Delivery agent compounds of the present invention include compounds as shown below and pharmaceutically acceptable salts thereof:

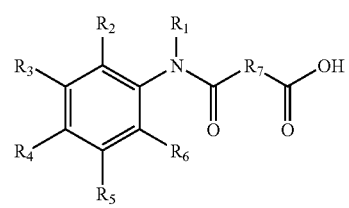

Formula E wherein:
R₁ is —(CH₂)$_m$—R₈, wherein m=0 or 1;
R₂-R₆ are independently selected from hydrogen, hydroxyl, halogen, C₁-C₄ alkyl, C₂-C₄ alkenyl, C₂-C₄ alkynyl, C₁-C₄ alkoxy, and cyano;
R₇ is selected from C₁-C₁₀ alkyl, C₂-C₁₀ alkenyl, and C₂-C₁₀ alkynyl;
R₈ is selected from cyclopentyl, cyclohexyl and phenyl, wherein when R₈ is a phenyl, m=1; and
R₈ is optionally substituted with C₁-C₄ alkyl, C₁-C₄ alkoxy, halogen or hydroxyl, or a combination thereof.
Other delivery agent compounds of the present invention include those of the formula:

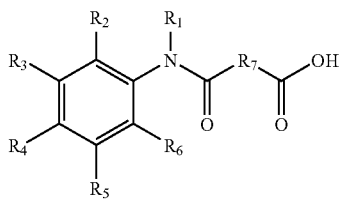

Formula F and pharmaceutically acceptable salts thereof, wherein:
R₁ is a C₁-C₆ alkyl, or C₂-C₆ alkenyl,
R₂-R₆ are independently chosen from the group consisting of hydrogen, hydroxyl, halogen, C₁-C₄ alkyl, C₂-C₄ alkenyl, C₂-C₄ alkynyl, C₁-C₄ alkoxy, and cyano, and
R₇ is selected from the group consisting of C₁-C₁₀ alkyl, C₂-C₁₀ alkenyl, and C₂-C₁₀ alkynyl.
Other delivery agent compounds of the present invention include those of the formula:

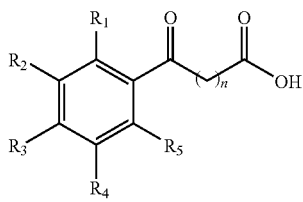

Formula G and pharmaceutically acceptable salts thereof, wherein
n=1 to 9, and
R₁ to R₅ are independently hydrogen, C₁ to C₄ alkyl, C₁ to C₄ alkoxy, C₂ to C₄ alkenyl, halogen, hydroxyl, —NH—C(O)—CH₃, or —O—C₆H₅.
Other delivery agent compounds of the present invention include those of the formula:

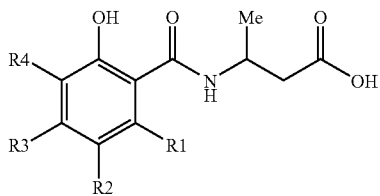

Formula H and pharmaceutically acceptable salts thereof, wherein
R₁ to R₄ are independently hydrogen, C₁ to C₄ alkyl, C₂ to C₄ alkenyl, halogen, C₁ to C₄ alkoxy, or hydroxyl.

Other delivery agent compounds of the present invention include those of the formula:

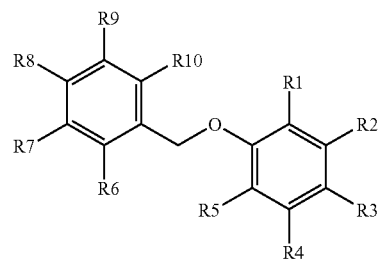

Formula I and pharmaceutically acceptable salts thereof, wherein
one of R1 to R5 has the generic structure

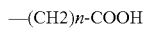
—(CH2)$n$-COOH where n=0-6;
the remaining four members of R₁ to R₅ are independently hydrogen, C₁ to C₄ alkyl, C₂ to C₄ alkenyl, halogen, C₁ to C₄ alkoxy, or hydroxyl; and
R₆-R₁₀ are independently hydrogen, C₁ to C₄ alkyl, C₂ to C₄ alkenyl, halogen, C₁ to C₄ alkoxy, or hydroxyl.

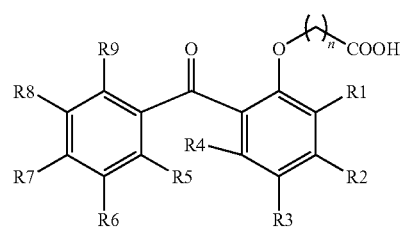

Formula J and pharmaceutically acceptable salts thereof, wherein
n=1 to 9; and
R₁ to R₉ are independently hydrogen, C₁ to C₄ alkyl, C₂ to C₄ alkenyl, halogen, C₁ to C₄ alkoxy, or hydroxyl.
Other delivery agent compounds of the present invention include those of the formula:

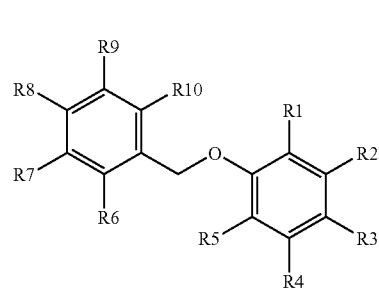

Formula K and pharmaceutically acceptable salts thereof, wherein
R₁-R₅ are independently hydrogen, C₁ to C₄ alkyl, C₂ to C₄ alkenyl, halogen, C₁ to C₄ alkoxy, hydroxyl, or —O—(CH2)n-COOH (where n is 1 to 12);
at least one of R₁ to R₅ has the generic structure

—O—(CH2)$n$-COOH where n=1-12; and
R₆-R₁₀ are independently hydrogen, C₁ to C₄ alkyl, C₂ to C₄ alkenyl, halogen, C₁ to C₄ alkoxy, or hydroxyl. International Application Nos. PCT/US2005/017339 and PCT/US2005/017309, filed May 16, 2005 and their priority documents, U.S. Provisional Application No. 60/576,088, filed Jun. 1, 2004, U.S. Provisional Application No. 60/576, 397, filed Jun. 1, 2004, U.S. Provisional Application No. 60/576,105, filed Jun. 1, 2004, U.S. Provisional Application No. 60/571,090, filed May 14, 2004, U.S. Provisional Application No. 60/571,092, filed May 14, 2004, U.S. Provisional Application No. 60/571,195, filed May 14, 2004, U.S. Provisional Application No. 60/571,194, filed May 14, 2004, U.S. Provisional Application No. 60/571,093, filed May 14, 2004, U.S. Provisional Application No. 60/571,055, filed May 14, 2004, U.S. Provisional Application No. 60/571,151, filed May 14, 2004, U.S. Provisional Application No. 60/571,315, filed May 14, 2004, U.S. Provisional Application No. 60/571,144, filed May 14, 2004, and U.S. Provisional Application 60/571,089, filed May 14, 2004, are hereby incorporated by reference in their entirety.

Also provided is a topical unit dosage form comprising the composition of the present invention. The topical unit dosage form will typically include a physiologically acceptable vehicle. For example, the topical composition or unit dosage form of the present invention can be an aqueous, semi-aqueous and oil-based solution or suspension. Suitable vehicles include, but are not limited to, water, isopropylmyristate (IPM), and polyethylene glycol (PEG) and water solutions. The topical composition or unit dosage form may be, for example, in the form of a cream, a gel, a lotion, an ointment, a suspension, or an emulsion (e.g. an oil-in-water emulsion).

Another embodiment is a method for administering a cromolyn component (e.g. cromolyn sodium), an analogue thereof, or a mixture thereof to an animal (e.g., a patient) in need thereof, by topically administering the composition or dosage unit form(s) of the present invention to the animal.

Yet another embodiment is a method of treating skin conditions, including but not limited to, atopic dermatitis and other eczematous disorders, mastocytosis, vernal deratoconjunctivitis, vernal conjunctivitis, vernal keratitis, skin wounds, skin infections, herpes simplex, herpes zoster, vaccinia virus or coxsackievirus, skin burns, decubitus ulcers, open sores, incisions, traumatic damage caused by irradiation of the skin, prevention of keloid scars and other scar tissue, vulvar vestibulitis, interstitial cystitis, vulvar vaginitis or vaginitis dynea, psoriasis, uremic pruritus, hemangioma, allergic rhinitis (hay fever), and "sinus" headaches in an animal in need thereof (e.g., a patient) by administering an effective amount of the composition or dosage unit form(s) of the present invention to the animal.

Yet another embodiment is a method of preparing a composition of the present invention by mixing at least one delivery agent compound and at least one cromolyn component.

BRIEF DESCRIPTION OF THE DRAWINGS

FIG. 1 is a graph of the percutaneous absorption of $^3$H-cromoglycate through human cadaver skin, after topical application of cromolyn sodium with or without the delivery agent SNAC (Formulation A) and 8-(2-Hydroxybenzoylamino)-octanoic acid 2-{2-[2-(2-{2-[2-(2-methoxyethoxy)ethoxy]ethoxy}-ethoxy)ethoxy]ethoxy}ethyl ester (Formulation B) as described in Examples 1-3 versus time.

FIGS. 2 and 3 are graphs of the percutaneous absorption of $^3$H-cromoglycate through human cadaver skin of Formulations A-C and D-F as described in Example 4 versus time.

FIGS. 4 and 5 are graphs of the percutaneous absorption of $^3$H-cromoglycate through human cadaver skin, of Formulations A-C and D-F as described in Example 5 versus time.

FIGS. 6 and 7 are graphs of the percutaneous absorption of $^3$H-cromoglycate through human cadaver skin, of Formulations A-C and D2-F2 as described in Example 6 versus time.

FIG. 8 are graphs of the average percutaneous absorption of $^3$H-cromoglycate through human cadaver skin of Formulations A-C in Examples 4-6 versus time.

FIG. 9 is a graph of the percutaneous absorption of $^3$H-cromoglycate through human cadaver skin, of Formulations A-C as described in Example 8 over time.

FIG. 10 is a graph of the percutaneous absorption of $^3$H-cromoglycate through human cadaver skin, of Formulations A-C as described in Example 8 and determined by a liquid scintillation counting technique versus time.

DETAILED DESCRIPTION OF THE INVENTION

Definitions

The term "hydrate" as used herein includes, but is not limited to, (i) a substance containing water combined in the molecular form and (ii) a crystalline substance containing one or more molecules of water of crystallization or a crystalline material containing free water.

The term "solvate" as used herein includes, but is not limited to, a molecular or ionic complex of molecules or ions of a solvent with molecules or ions of the delivery agent compound or salt thereof, or hydrate or solvate thereof.

The term "delivery agent" refers to any of the delivery agent compounds disclosed herein.

The term "SNAC" refers to the monosodium salt of N-(8-[2-hydroxybenzoyl]-amino)caprylic acid.

The term "SNAD" refers to the monosodium salt of N-(10-[2-hydroxybenzoyl]-amino)decanoic acid. The term "disodium salt of SNAD" refers to the disodium salt of N-(10-[2-hydroxybenzoyl]-amino)decanoic acid.

An "effective amount of the cromolyn component" is an amount of the cromolyn component which is effective to treat or prevent the condition for which it is administered in a living organism over some period of time, e.g., an amount which provides a therapeutic effect. Indications for which a cromolyn component is administered are known to those skilled in the art, some of which are disclosed herein, and also include those conditions that can be treated or prevented with a cromolyn component which are to be later discovered.

An "effective amount of delivery agent" is an amount of the delivery agent which enables and/or facilitates an increased concentration of the cromolyn component in the epidermis layer of the skin, as compared the concentration of the cromolyn component in the epidermis upon administration of the cromolyn component without the delivery agent.

The term "mean", when preceding a pharmacokinetic value (e.g., mean Peak) represents the arithmetic mean value of the pharmacokinetic value unless otherwise specified.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

The term "about" generally means within 10%, preferably within 5%, and more preferably within 1% of a given value or range.

The terms "alkyl" and "alkenyl" as used herein include linear and branched alkyl and alkenyl substituents, respectively.

The term "patient" as used herein refers to a mammal and preferably a human.

The phrase "pharmaceutically acceptable" refers to additives or compositions that are physiologically tolerable and do not typically produce an allergic or similar untoward reaction, such as rash, welts, swelling, increased sensitivity, and the like, when administered to the skin or nasal membrane of a patient.

Cromolyn Component

The term cromolyn component as used herein includes salts (i.e. cromoglycates) and free base forms of cromoglycic acid, along with their analogues. Cromoglycic acid is commonly referred to as cromolyn. A preferred salt is disodium cromoglycate, commonly referred to as cromolyn sodium. Analogues of cromoglycic acid include, but are not limited to, those disclosed in U.S. Pat. No. 3,419,578, which is hereby incorporated by reference. The cromolyn analogues include those which possess anti-PAR-2 (protease-activated receptor-2) characteristics.

Methods of preparing cromolyn and its analogues are described in U.S. Pat. No. 3,419,578, which is hereby incorporated by reference.

Delivery Agent Compounds

The delivery agent compound may be any of those described in U.S. Pat. Nos. 6,846,844, 6,699,467, 6,693,208, 6,693,208, 6,693,073, 6,663,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 5,541,155, 5,693,338, 5,976,569, 5,643,957, 5,955,503, 6,100,298, 5,650,386, 5,866,536, 5,965,121, 5,989,539; 6,001,347, 6,071,510, and 5,820,881; U.S. Published Application Nos. 20050009748, 20040110839, 20040106825, 20040068013, 20040062773, 20040022856, 20030235612, 20030232085, 20030225300, 20030198658, 20030133953, 20030078302, 20030072740, 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, 20010003001 International Publication Nos. WO 2005/020925, WO 2004/104018, WO 2004/080401, WO 2004/062587, WO 2003/057650, WO 2003/057170, WO 2003/045331, WO 2003/045306, WO 2003/026582, WO 2002/100338, WO 2002/070438, WO 2002/069937, WO 02/20466, WO 02/19969, WO 02/16309, WO 02/15959, WO 02/02509, WO 01/92206, WO 01/70219, WO 01/51454, WO 01/44199, WO 01/34114, WO 01/32596, WO 01/32130, WO 00/07979, WO 00/59863, WO 00/50386, WO 00/47188, WO 00/40203, and WO 96/30036, all of which are hereby incorporated by reference in their entirety.

Non-limiting examples of delivery agent compounds include N-(8-[2-hydroxybenzoyl]-amino)caprylic acid, N-(10-[2-hydroxybenzoyl]-amino)decanoic acid, 8-(2-hydroxy-4-methoxybenzoylamino)octanoic acid, 4-[(2-hydroxy-4-chlorobenzoyl)amino]butanoate, 8-(2,6-dihydroxybenzoylamino)octanoic acid, 8-(2-hydroxy-5-bromobenzoylamino)octanoic acid, 8-(2-hydroxy-5-chlorobenzoylamino)octanoic acid, 8-(2-hydroxy-5-iodobenzoylamino)octanoic acid, 8-(2-hydroxy-5-methylbenzoylamino)octanoic acid, 8-(2-hydroxy-5-fluorobenzoylamino)octanoic acid, 8-(2-hydroxy-5-methoxybenzoylamino)octanoic acid, 8-(3-hydroxyphenoxy)octanoic acid, 8-(4-hydroxyphenoxy) octanoic acid, 6-(2-cyanophenoxy)hexanoic acid, 8-(2-Hydroxyphenoxy)octyl-diethanolamine, 8-(4-hydroxyphenoxy)octanoate, 8-(4-hydroxyphenoxy) octanoate, 8-(2-hydroxy-4-methoxybenzoylamino)octanoic acid, 8-(2-hydroxy-5-methoxybenzoylamino)-octanoic acid, and salts thereof. Preferred salts include, but are not limited to, monosodium and disodium salts.

The delivery agent compounds may be in the form of the carboxylic acid or pharmaceutically acceptable salts thereof, such as sodium salts, and hydrates and solvates thereof. The salts may be mono- or multivalent salts, such as monosodium salts and disodium salts. The delivery agent compounds may contain different counter ions chosen for example due to their effect on modifying the dissolution profile of the carrier.

The delivery agent compounds may be prepared by methods known in the art, such as those discussed in the aforementioned publications (e.g., International Publication Nos. WO 98/34632, WO 00/07979, WO 01/44199, WO 01/32596, WO 02/20466, and WO 03/045306). SNAC, SNAD, and the free acid and other salts thereof may be prepared by any method known in the art, such as those described in U.S. Pat. Nos. 5,650,386 and 5,866,536.

Salts of the delivery agent compounds of the present invention may be prepared by methods known in the art. For example, sodium salts may be prepared by dissolving the delivery agent compound in ethanol and adding aqueous sodium hydroxide.

The delivery agent compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

In one embodiment, the weight ratio of delivery agent to cromolyn component ranges from about 0.1:1 to about 2000:1. The weight ratio may vary according to the cromolyn component delivered and the particular indication for which it is administered.

Delivery Systems

The composition of the present invention comprises one or more delivery agent compounds of the present invention and/or one or more cromolyn component. The delivery agent compound and cromolyn component are typically mixed prior to administration to form an administration composition (which may comprise a unit dosage form).

The administration composition may include one or more cell stimulating compounds, such as those described in U.S. Pat. No. 6,573,249 which is incorporated by reference. Cell stimulating compounds include human growth hormone, insulin (containing transferrin or transferrin-free) and/or triiodothyronine or thyroxin.

The administration composition may also contain other active ingredients such as those discussed in International Publication No. 99/60997 which is hereby incorporated by reference, anti-allergic medications (e.g. oxatamide), glucocorticoids or corticosteroids (e.g. betamethasone valerate, triamcinolone acetonide, clobetasone butyrate, hydrocortisone and triamcinolone).

The administration composition may also contain other ingredients known to provide therapeutic effects to skin. These ingredients include, but are not limited to, aloe, antioxidants, moisturizers or humectants, vitamins, surfactants, hydroxy acids, proteolytic enzymes, skin lightening agents (e.g. melanin inhibitors, melanin bleaches), sunscreen, colorants, perfumes, preservatives, pigments, antiseptic agents, and toners. Any of the ingredients listed in the *International Cosmetic Ingredient Dictionary and Handbook*, 9$^{th}$ Ed. 2002, by The Cosmetic Toiletry Fragrance Association (ISBN 1882621298), which is hereby incorporated by reference in its entirety, may be incorporated into the administration composition of the present invention.

The administration composition is typically applied topically to a targeted area of skin. The administration composition may be applied daily, for typically at least several days. However, more frequent application is also contemplated. For example, in the treatment of injured tissue, such as a rash, or an allergy-induced skin problem, it may be desirable to continuously maintain the administration composition on the affected area during healing, with applications of the administration composition from two to four times a day or more frequently. Use may also be for extended periods, including years.

Embodiments of the present invention include a cream or ointment base. This is particularly true where the composition is used on dry or peeling skin and when a moisturizing vehicle may otherwise be desirable. Suitable bases include lanolin, SILVADENE™ (silver sulfadiazine) (Hoechst Marion Roussel, Kansas City, Mo.), particularly for treatment of burns, AQUAPHOR™ (Duke Laboratories, South Norwalk, Conn.), and like bases.

Viscosity building agents can be added to aqueous or oil based solutions to form a cream or gel. Examples of viscosity building agents include such as gelatin, chitosan and its derivatives, hydrophilic cellulose (preferably a hydroxyalkylcellulose and more preferably, hydroxymethylcellulose, hydroxyethylcellulose, or the like or a mixture thereof), and polyacrylate-polyacrylic acid polymers (e.g., Carbomers and the like).

If desired, it is possible to incorporate either aqueous or water-oil base compositions in bandages or other wound dressings to provide for continuous exposure of the affected area to the topical composition. Aerosol applicators may also find use.

The amount of the cromolyn component in the administration composition is an effective amount of cromolyn component, which can be determined by those skilled in the art depending on the condition for which it is administered. The unit dosage form may comprise, for example, from about 0.01% to 10%, or about 0.01% to about 7%, or about 0.5% to about 4.0% of the cromolyn component (e.g. cromolyn sodium). In alternative embodiments, a cromolyn component is added until the administration composition is saturated with the cromoglycic acid compound. In aqueous vehicles, this may correlate to a cromoglycic acid compound concentration of about 5%. In semi-aqueous vehicles, such as isopropylmyristate, this may correlate to about 0.01% cromolyn component concentration. In other vehicles, such as a PEG/Water vehicle, the cromolyn component concentration is about 3% upon saturation of the administration composition.

The present invention provides, in addition to compositions as described above, a method for improving skin conditions. The method comprises applying the topical composition to an affected area. Atopic dermatitis and other eczematous disorders, skin wounds, skin infections, herpes simplex, herpes zoster, vaccinia virus or coxsackievirus, skin burns, decubitus ulcers, open sores, incisions, traumatic damage caused by irradiation of the skin, prevention of keloid scars and other scar tissue, vulvar vestibulitis, interstitial cystitis, vulvar vaginitis or vaginitis dynea, psoriasis, uremic pruritus, hemangioma, allergic rhinitis (hay fever), and "sinus" headaches can be treated or prevented by administering an effective amount of the composition or dosage unit form(s) of the present invention to the animal.

EXAMPLES

The following examples illustrate the invention without limitation. All parts are given by weight unless otherwise indicated.

Example 1

Human Cadaver Skin Model and Dosing

The in vitro human cadaver skin model has proven to be a valuable tool for the study of percutaneous absorption and the determination of the pharmacokinetics of topically applied excipients and/or drugs. The model uses human cadaver skin mounted in specially designed diffusion chambers which allow the skin to be maintained at a temperature and humidity that match typical in vivo conditions (See Franz, Percutaneous absorption: On the Relevance of in vitro data, *J Invest Derm.*, 64:190-195 (1975)). Typically a finite dose of formulation is applied to the outer surface of the skin and absorption of the compound of interest is measured by monitoring its rate of appearance in the receptor solution bathing the inner surface of the skin. Data defining total absorption, rate of absorption, as well as skin content can be accurately determined in this model. The method has historic precedent for accurately predicting in vivo percutaneous absorption kinetics (See Franz T. J., Skin: Drug Application and Evaluation of Environmental Hazards, *Current Problems in Dermatology*, 7:58-68 (1978).

Human cadaver obtained within 24 hours of death, or surgically excised trunk skin without obvious signs of skin disease were used in these examples. Skin was cleared of subcutaneous tissue and approximately 50% of the dermis by scalpel. As received, the skin is sealed in a water-impermeable plastic bag, having been shipped on wet ice. If not used on the day of arrival, the skin was stored at <−70° C. until the day of the experiment. Prior to use it was thawed by placing the bag in ~37° C. water, then rinsed in tap water to remove any adherent blood or other material from the surface.

Skin from a single donor was cut into multiple smaller sections large enough to fit onto 0.8 cm$^2$ Franz diffusion cells (Crown Glass Co., Somerville, N.J.). Skin thickness was measured and recorded. The receptor chamber was filled to capacity with a receptor solution of phosphate-buffered isotonic saline (PBS), pH 7.4±0.1, and the donor chamber was left open to the ambient laboratory environment. The cells were then placed in a diffusion apparatus in which the receptor solution is stirred magnetically at ~600 RPM and which is maintained to achieve a skin surface temperature of 33.0±1.0° C. Skin surface temperatures from representative chambers were measured and recorded.

To assure the integrity of each skin section, its permeability to tritiated water was determined before application of the test products (See Franz T. J., The use of water permeability as a means of validation for skin integrity in in vitro percutaneous absorption studies, *Abst. J Invest Dermatol.* 94:525 (1990)) Following a brief (0.5-1 hour) equilibrium period, $^3H_2O$ (NEN, Boston, Mass., sp. Act. ~0.5 µCi/mL) was layered across the top of the skin by dropper so that the entire exposed surface is covered (approximately 100-150 µL). After 5 minutes the $^3H_2O$ aqueous layer was removed. At 30 minutes the receptor solution was collected and analyzed for radioactive content by liquid scintillation counting. Skin specimens in which absorption of $^3H_2O$ was less than 1.25 µL-equ were considered acceptable.

Prior to administration of the topical test formulations to the skin sections, the receptor solution was replaced with fresh PBS solution prior to dosing. All formulations were then applied to the skin sections using a positive displacement pipette set to deliver 5 µL (5 µL/0.8 cm$^2$). The dose was spread throughout the surface with the Teflon tip of the pipette. Five to ten minutes after application the chimney portion of the Franz Cell was replaced.

Example 2

Test Formulations and Analytical Methods

Radiolabeled Cromoglycate, characterized as Di-sodium [3H]-cromoglycate, was received from Amersham Biosciences (part of GE Healthcare, Piscataway, N.J.). Each formulation below was spiked with 20-25 µL/mL of the radiolabeled Di-sodium [3H]-cromoglycate to obtain quantifiable counts in the samples. Final specific activity and isotope concentration of each formulation was determined experimentally by liquid scintillation counting and the manufacturer's stated specific activity.

From the receptor solution samples, surface wash, and dissolved skin, an aliquot of each sample was mixed with 5 mL scintillation fluid (ScintiVerse, Fisher Scientific). All samples were then assayed for isotope content by liquid scintillation counting using a Packard LSC1900 Scintillation Counter. Counts per minutes (CPM) were automatically converted to disintegrations per minute (DPM), by the instrument, using an external standard quench correction curve. All calculations of flux, skin content, surface wash recovery, and mass balance were made on the basis of the experimentally determined values for specific activity.

All samples from Examples 4, 5, and 6 were counted for 10 minutes, in duplicate, per sample. The average background for all the un-dosed chamber samples was used in the final calculations. The average background count was found to be 52.9±12.5 DPM. For calculation purposes, any sample less than the mean background was entered as 52.9 DPM (to prevent negative penetration values).

The samples from Example 3 were counted for 5 minutes, in duplicate, per sample. The average background used was equivalent to the water background and was set at 22.04 DPM.

The following test formulations were prepared and tested.

TABLE 1

Composition of Evaluated Formulations

| Formulation | Drug Concentration (wt %) | Carrier Concentration (wt %) | Specific Activity (DPM/µL) | Formulation vehicle |
|---|---|---|---|---|
| A | 5.03 | 0 | 33618.1 | Water (pH~8) |
| B | 5.08 | 3 A | 32966.6 | Water (pH~8) |
| C | 4.94 | 15 B | 31862.1 | Water (pH~8) |
| D | 0.011 | 0 | 27955.2 | IPM |
| E | 0.013 | 2.4 A | 29165.8 | IPM |
| F | 0.007 | 12 B | 20960.2 | IPM |
| D2 | 3.06 | 0 | 49720.5 | 15:85 PEG/Water |
| E2 | 3.06 | 3 A | 43484.9 | 15:85 PEG/Water |
| F2 | 3.16 | 15 B | 38378.1 | 15:85 PEG/Water |

Carrier A is the mono-sodium salt of N-(8-[2-hydroxybenzoyl]-amino)caprylic acid SNAC).
Carrier B is 8-(2-Hydroxybenzoylamino)-octanoic acid 2-{2-[2-(2-{2-[2-(2-methoxyethoxy)ethoxy]ethoxy}-ethoxy)ethoxy]ethoxy}ethyl ester.

At pre-selected times after dosing, the receptor solution was removed in its entirety, replaced with fresh receptor solution, and a 1 mL volume aliquot saved for subsequent analysis. Aliquots were mixed with scintillation fluid and counted.

Following the last scheduled receptor solution collection, the skin was washed with ethanol to collect any un-absorbed formulation from the surface of the skin. The skin sections were separated into epidermis and dermis. Each separate epidermis and dermis was mixed with 0.5 mL Soluene-350 (Packard Chemical Co.) and allowed to dissolve for approximately 48 hours at room temperature. Once dissolved these samples were mixed with scintillation fluid and counted.

After a given time period, the percentage of 3H-Cromoglycate found on the surface (surface wash), epidermis layer, dermis layer, and receiver compartment (amount which traversed the dermis layer), as compared to the total amount applied, was determined.

Example 3

Analysis of Formulations A and B

Formulations A and B were applied over 48 hours to 1 donor. The specific activity of each formulation was calculated, and it was noted that each formulation was not sufficiently spiked with 3H-cromoglycate. Thus, each formulation was spiked with additional radiolabeled isotope and the specific activity was recalculated. The skin sections for each formulation were re-dosed with the newly spiked formulations four hours after they were initially dosed.

The following results were obtained:

TABLE 2

Mean Flux (µg/cm$^2$/hr) Results: $^3$H-Cromoglycate Study #1 Summary Percutaneous Absorption of $^3$H-Cromoglycate through Human Skin in vitro, over 48 hours, from a Single Dose Application (Mean ± SD, n = 1 Donor).

| Time (hr)* | A | B |
|---|---|---|
| 1 | 0.281 ± 0.141 | 0.234 ± 0.023 |
| 3 | 0.248 ± 0.068 | 0.265 ± 0.050 |
| 6 | 0.227 ± 0.216 | 0.129 ± 0.016 |
| 9 | 0.305 ± 0.126 | 0.245 ± 0.053 |
| 11 | 0.338 ± 0.180 | 0.247 ± 0.005 |

TABLE 2-continued

Mean Flux (μg/cm²/hr) Results: ³H-Cromoglycate Study #1 Summary Percutaneous Absorption of ³H-Cromoglycate through Human Skin in vitro, over 48 hours, from a Single Dose Application (Mean ± SD, n = 1 Donor).

| Time (hr)* | A | B |
|---|---|---|
| 18 | 0.087 ± 0.084 | 0.036 ± 0.011 |
| 28 | 0.094 ± 0.052 | 0.064 ± 0.007 |
| 40 | 0.059 ± 0.029 | 0.032 ± 0.013 |

*Time as midpoint between samples.

This data is shown in FIG. 1.

TABLE 3

³H-Cromoglycate Mass Balance Summary Percutaneous Absorption of ³H-Cromoglycate applied to Human Skin in vitro, over 48 hours, from a Single Dose Application (n = 1 Donor). Mean ± SD as Percent of Applied Dose and Total Mass (μg).

| Parameter | A | B |
|---|---|---|
| Receiver Compartment (%) | 1.902 ± 1.186 | 1.241 ± 0.032 |
| Receiver Compartment (μg) | 4.784 ± 2.984 | 3.153 ± 0.080 |
| Dermis (%) | 1.881 ± 2.358 | 4.840 ± 2.992 |
| Epidermis (%) | 26.613 ± 11.634 | 44.383 ± 40.970 |
| Surface Wash (%) | 31.548 ± 1.399 | 8.616 ± 1.690 |
| Total Recovery (%) | 61.944 ± 13.769 | 69.080 ± 39.700 |

Because Example 3 only included formulations A and B, and due to re-dosing of the skin sections, these results were not used in the overall calculations shown in Example 9.

Example 4

First Analysis of Formulations A, B, C, D, E, and F

Example 4 was conducted using Formulations A, B, C, D, E, and F. The receptor solution sampling times were 4, 7, 19, 24, 27, and 43 hours post dose.

TABLE 4

Mean Flux (μg/cm²/hr) Results: ³H-Cromoglycate Study Percutaneous Absorption of ³H-Cromoglycate through Human Skin in vitro, over 48 hours, from a Single Dose Application (Mean ± SD, n = 1 Donor).

| Time (hr)* | A | B | C |
|---|---|---|---|
| 2 | 0.185 ± 0.161 | 0.803 ± 0.848 | 1.477 ± 1.626 |
| 5.5 | 0.000 ± 0.000 | 0.014 ± 0.024 | 0.139 ± 0.162 |
| 13 | 0.000 ± 0.000 | 0.000 ± 0.000 | 0.025 ± 0.024 |
| 21.5 | 0.003 ± 0.005 | 0.000 ± 0.000 | 0.003 ± 0.005 |
| 25.5 | 0.000 ± 0.000 | 0.000 ± 0.000 | 0.000 ± 0.000 |
| 35 | 0.000 ± 0.000 | 0.000 ± 0.000 | 0.056 ± 0.096 |

*Time as midpoint between samples.

These results are shown in FIG. 2.

TABLE 5

Mean Flux (ng/cm²/hr) Results: ³H-Cromoglycate Summary Percutaneous Absorption of ³H-Cromoglycate through Human Skin in vitro, over 48 hours, from a Single Dose Application (Mean ± SD, n = 1 Donor).

| Time (hr)* | D | E | F |
|---|---|---|---|
| 2 | 1.889 ± 2.694 | 0.000 ± 0.000 | 0.217 ± 0.209 |
| 5.5 | 0.163 ± 0.282 | 0.000 ± 0.000 | 0.058 ± 0.096 |
| 13 | 0.028 ± 0.046 | 0.000 ± 0.000 | 0.005 ± 0.008 |
| 21.5 | 0.020 ± 0.035 | 0.000 ± 0.000 | 0.004 ± 0.008 |
| 25.5 | 0.053 ± 0.092 | 0.000 ± 0.000 | 0.000 ± 0.000 |
| 35 | 0.050 ± 0.081 | 0.000 ± 0.000 | 0.004 ± 0.007 |

*Time as midpoint between samples.

These results are shown in FIG. 3.

TABLE 6

³H-Cromoglycate Mass Balance Summary: Percutaneous Absorption of ³H-Cromoglycate applied to Human Skin in vitro, over 48 hours, from a Single Dose Application (n = 1 Donor). Mean ± SD as Percent of Applied Dose and Total Mass (ng).

| Parameter | D | E | F |
|---|---|---|---|
| Receiver Compartment (%) | 1.375 ± 2.024 | 0.000 ± 0.000 | 0.272 ± 0.170 |
| Receiver Compartment (ng) | 7.561 ± 11.130 | 0.000 ± 0.000 | 0.953 ± 0.596 |
| Dermis (%) | 0.395 ± 0.256 | 0.044 ± 0.021 | 1.790 ± 1.451 |
| Epidermis (%) | 2.409 ± 0.881 | 2.152 ± 0.116 | 27.071 ± 2.347 |
| Surface Wash (%) | 55.032 ± 37.483 | 72.458 ± 7.079 | 90.753 ± 6.209 |
| Total Recovery (%) | 59.211 ± 38.899 | 74.654 ± 7.004 | 119.886 ± 5.069 |

TABLE 7

³H-Cromoglycate Study #2 Mass Balance Summary: Percutaneous Absorption of ³H-Cromoglycate applied to Human Skin in vitro, over 48 hours, from a Single Dose Application (n = 1 donor). Mean ± SD as Percent of Applied Dose and Total Mass (μg).

| Parameter | A | B | C |
|---|---|---|---|
| Receiver Compartment (%) | 0.239 ± 0.204 | 1.024 ± 1.089 | 2.436 ± 2.830 |
| Receiver Compartment (μg) | 0.602 ± 0.513 | 2.602 ± 2.767 | 6.021 ± 6.993 |
| Dermis (%) | 0.167 ± 0.111 | 0.473 ± 0.727 | 0.886 ± 0.919 |
| Epidermis (%) | 4.940 ± 1.793 | 11.544 ± 10.850 | 2.339 ± 2.137 |
| Surface Wash (%) | 30.635 ± 1.330 | 33.758 ± 0.229 | 34.418 ± 2.021 |
| Total Recovery (%) | 35.981 ± 2.040 | 46.799 ± 9.759 | 40.079 ± 2.860 |

Example 5

Second Analysis of Formulations A, B, C, D, E, and F

Example 5 was conducted using Formulations A, B, C, D, E, and F. The sampling times were 6, 12, 24, 27, and 43 hours post dose.

TABLE 8

Mean Flux (µg/cm²/hr) Results: ³H-Cromoglycate Summary
Percutaneous Absorption of ³H-Cromoglycate through Human Skin
in vitro, over 48 hours, from a Single Dose Application (Mean ± SD,
n = 1 Donor).

| Time (hr)* | A | B | C |
|---|---|---|---|
| 3 | 0.007 ± 0.012 | 0.168 ± 0.147 | 0.701 ± 0.920 |
| 9 | 0.000 ± 0.000 | 0.008 ± 0.013 | 0.046 ± 0.068 |
| 18 | 0.000 ± 0.000 | 0.003 ± 0.005 | 0.004 ± 0.007 |
| 36 | 0.000 ± 0.000 | 0.004 ± 0.007 | 0.018 ± 0.023 |

*Time as midpoint between samples.

These results are shown in FIG. 4.

TABLE 9

³H-Cromoglycate Mass Balance Summary
Percutaneous Absorption of ³H-Cromoglycate applied to Human
Skin in vitro, over 48 hours, from a Single Dose Application
(n = 1 Donor). Mean ± SD as Percent of Applied Dose
and Total Mass (µg).

| Parameter | A | B | C |
|---|---|---|---|
| Receiver Compartment (%) | 0.013 ± 0.023 | 0.378 ± 0.329 | 1.603 ± 1.926 |
| Receiver Compartment (µg) | 0.033 ± 0.058 | 0.960 ± 0.836 | 3.962 ± 4.759 |
| Dermis (%) | 0.025 ± 0.010 | 0.482 ± 0.419 | 1.320 ± 1.821 |
| Epidermis (%) | 0.558 ± 0.190 | 2.395 ± 3.413 | 1.622 ± 1.186 |
| Surface Wash (%) | 31.650 ± 1.165 | 28.059 ± 6.768 | 30.765 ± 0.719 |
| Total Recovery (%) | 32.246 ± 1.070 | 31.314 ± 10.515 | 35.309 ± 4.544 |

TABLE 10

Mean Flux (ng/cm²/hr) Results: ³H-Cromoglycate
Summary Percutaneous Absorption of ³H-Cromoglycate
through Human Skin in vitro over 48 hours from a Single Application
(Mean ± SD, n = 1 Donor).

| Time (hr)* | D | E | F |
|---|---|---|---|
| 3 | 1.600 ± 2.385 | 0.042 ± 0.072 | 0.072 ± 0.112 |
| 9 | 0.064 ± 0.110 | 0.000 ± 0.000 | 0.012 ± 0.021 |
| 18 | 0.006 ± 0.011 | 0.000 ± 0.000 | 0.023 ± 0.039 |
| 36 | 0.014 ± 0.024 | 0.000 ± 0.000 | 0.010 ± 0.018 |

*Time as midpoint between samples.

These results are shown in FIG. 5.

TABLE 11

³H-Cromoglycate Mass Balance Summary:
Percutaneous Absorption of ³H-Cromoglycate applied to
Human Skin in vitro over 48 hours from a Single Application.
Mean ± SD as Percent of Applied Dose and Total Mass (ng).

| Parameter | D | E | F |
|---|---|---|---|
| Receiver Compartment (%) | 1.510 ± 2.279 | 0.031 ± 0.053 | 0.235 ± 0.387 |
| Receiver Compartment (ng) | 8.309 ± 12.534 | 0.200 ± 0.347 | 0.821 ± 1.356 |
| Dermis (%) | 0.253 ± 0.199 | 0.037 ± 0.014 | 0.341 ± 0.300 |

TABLE 11-continued

³H-Cromoglycate Mass Balance Summary:
Percutaneous Absorption of ³H-Cromoglycate applied to
Human Skin in vitro over 48 hours from a Single Application.
Mean ± SD as Percent of Applied Dose and Total Mass (ng).

| Parameter | D | E | F |
|---|---|---|---|
| Epidermis (%) | 1.951 ± 0.408 | 0.194 ± 0.048 | 13.995 ± 4.221 |
| Surface Wash (%) | 86.051 ± 16.074 | 7.946 ± 9.157 | 33.710 ± 5.421 |
| Total Recovery (%) | 89.765 ± 18.728 | 8.207 ± 9.162 | 48.281 ± 2.162 |

Example 6

Analysis of Formulations A, B, C, and D2, E2, and F2

Example 6 was conducted using Formulations A, B, C, D, E, and F. Two donors were evaluated for formulations A, and B, and three donors were evaluated for formulations C, D2, E2, and F2. The receptor solution sampling times for formulations A, B, and C were 0.5, 2, 4, 6, and 8 hours post dose. At 8 hours, these chambers were surface washed and the skin selections collected. The sampling times for formulations D2, E2, and F2 were 0.5, 2, 4, 6, 8, 12, 24, 32, and 48 hours post dose. At 48 hours, these chambers were surface washed and the skin sections collected.

TABLE 12

Mean Flux (µg/cm²/hr) Results: ³H-Cromoglycate
Summary
Percutaneous Absorption of ³H-Cromoglycate through Human Skin
in vitro, over 8 hours, from a Single Dose Application (Mean ± SE,
n = 2 or 3 Donors).

| Time (hr)* | A | B | C |
|---|---|---|---|
| 0.25 | 0.317 ± 0.101 | 0.000 ± 0.000 | 0.154 ± 0.080 |
| 1.25 | 0.030 ± 0.030 | 0.000 ± 0.000 | 0.036 ± 0.030 |
| 3 | 0.004 ± 0.003 | 0.000 ± 0.000 | 0.017 ± 0.017 |
| 5 | 0.001 ± 0.001 | 0.001 ± 0.001 | 0.018 ± 0.012 |
| 7 | 0.001 ± 0.001 | 0.008 ± 0.008 | 0.000 ± 0.000 |
| Number of donors (n) | 2 | 2 | 3 |

*Time as midpoint between samples.

These results are shown in FIG. 6.

TABLE 13

³H-Cromoglycate Mass Balance Summary
Percutaneous Absorption of ³H-Cromoglycate applied to Human
Skin in vitro, over 8 hours, from a Single Dose Application.
Mean ± SE as Percent of Applied Dose and Total Mass (µg).

| Parameter | A | B | C |
|---|---|---|---|
| Receiver Compartment (%) | 0.068 ± 0.033 | 0.006 ± 0.006 | 0.065 ± 0.038 |
| Receiver Compartment (µg) | 0.171 ± 0.084 | 0.015 ± 0.015 | 0.161 ± 0.094 |
| Dermis (%) | 0.100 ± 0.093 | 0.027 ± 0.002 | 0.967 ± 0.795 |
| Epidermis (%) | 5.545 ± 0.157 | 5.935 ± 5.419 | 16.852 ± 10.870 |
| Surface Wash (%) | 46.138 ± 3.827 | 51.906 ± 1.045 | 53.802 ± 3.131 |
| Total Recovery (%) | 51.851 ± 3.925 | 57.874 ± 4.370 | 71.686 ± 14.820 |
| Number of Donors (n) | 2 | 2 | 3 |

TABLE 14

Mean Flux (ng/cm$^2$/hr) Results: $^3$H-Cromoglycate Summary
Percutaneous Absorption of $^3$H-Cromoglycate through Human Skin in vitro, over 48 hours, from a Single Application (Mean ± SE, n = 3 Donors).

| Time (hr)* | D2 | E2 | F2 |
|---|---|---|---|
| 0.25 | 0.392 ± 0.267 | 0.045 ± 0.041 | 0.465 ± 0.377 |
| 1.25 | 0.193 ± 0.142 | 0.013 ± 0.013 | 0.093 ± 0.044 |
| 3 | 0.084 ± 0.064 | 0.003 ± 0.003 | 0.055 ± 0.027 |
| 5 | 0.041 ± 0.025 | 0.001 ± 0.000 | 0.049 ± 0.024 |
| 7 | 0.018 ± 0.011 | 0.000 ± 0.000 | 0.036 ± 0.027 |
| 10 | 0.012 ± 0.008 | 0.000 ± 0.000 | 0.019 ± 0.014 |
| 18 | 0.014 ± 0.012 | 0.000 ± 0.000 | 0.018 ± 0.015 |
| 28 | 0.011 ± 0.009 | 0.000 ± 0.000 | 0.018 ± 0.015 |
| 40 | 0.011 ± 0.010 | 0.000 ± 0.000 | 0.013 ± 0.009 |

*Time as midpoint between samples.

These results are shown in FIG. 7.

TABLE 15

$^3$H-Cromoglycate Mass Balance Summary:
Percutaneous Absorption of $^3$H-Cromoglycate applied to Human Skin in vitro, over 48 hours, from a Single Dose Application.
Mean ± SE as Percent of Applied Dose and Total Mass (µg).

| Parameter | D2 | E2 | F2 |
|---|---|---|---|
| Receiver Compartment (%) | 0.663 ± 0.501 | 0.027 ± 0.024 | 0.660 ± 0.453 |
| Receiver Compartment (µg) | 1.004 ± 0.759 | 0.041 ± 0.037 | 1.040 ± 0.714 |
| Dermis (%) | 0.231 ± 0.062 | 0.123 ± 0.107 | 0.285 ± 0.202 |
| Epidermis (%) | 0.664 ± 0.169 | 1.892 ± 1.156 | 3.370 ± 2.763 |
| Surface Wash (%) | 69.364 ± 15.259 | 56.734 ± 20.174 | 71.055 ± 22.339 |
| Total Recovery (%) | 70.922 ± 15.575 | 58.776 ± 20.381 | 75.370 ± 19.620 |

Example 7

Summary of Examples 4-6 for Formulations A, B, and C

The results of the overall average of Examples 4-6 for the percutaneous absorption of $^3$H-Cromoglycate from formulations A, B, and C are summarized in FIG. 8, and Tables 16 and 17. Where different sample times and study durations occurred, the data was interpolated to allow for determination of the means across similar time durations.

TABLE 16

Mean Flux (µg/cm$^2$/hr) Results: $^3$H-Cromoglycate Overall Summary
Percutaneous Absorption of $^3$H-Cromoglycate through Human Skin in vitro, through 8 hours, from a Single Application (Mean ± SE, n = 5 Donors).

| Time (hr)* | A | B | C |
|---|---|---|---|
| 0.25 | 0.317 ± 0.101 | 0.000 ± 0.000 | 0.154 ± 0.080 |
| 1.25 | 0.030 ± 0.024 | 0.000 ± 0.000 | 0.036 ± 0.026 |
| 3 | 0.018 ± 0.012 | 0.106 ± 0.052 | 0.129 ± 0.106 |
| 5 | 0.001 ± 0.001 | 0.018 ± 0.010 | 0.106 ± 0.063 |
| 7 | 0.002 ± 0.002 | 0.030 ± 0.019 | 0.136 ± 0.124 |
| Number of Donors (n) | 4 | 4 | 5 |

*Time as midpoint between samples.

This data is shown in FIG. 8.

TABLE 17

$^3$H-Cromoglycate Mass Balance Overall Summary
Percutaneous Absorption of $^3$H-Cromoglycate applied to Human Skin in vitro, through 8 hours, from a Single Dose Application.
Mean ± SE as Percent of Applied Dose and Total Mass (µg).

| Parameter | A | B | C |
|---|---|---|---|
| Receiver Compartment (%) | 0.096 ± 0.045 | 0.342 ± 0.196 | 0.736 ± 0.424 |
| Receiver Compartment (µg) | 0.242 ± 0.113 | 0.870 ± 0.499 | 1.826 ± 1.047 |
| Dermis (%) | 0.098 ± 0.055 | 0.252 ± 0.106 | 1.021 ± 0.442 |
| Epidermis (%) | 4.147 ± 1.393 | 6.452 ± 2.376 | 10.904 ± 6.981 |
| Surface Wash (%) | 38.640 ± 5.319 | 41.407 ± 5.052 | 45.317 ± 5.502 |
| Total Recovery (%) | 42.981 ± 6.258 | 48.454 ± 5.343 | 57.981 ± 11.698 |
| Number of Donors (n) | 4 | 4 | 5 |

Example 8

Analysis of Formulations A, B, C

A study on a single donor was conducted using formulations A, B, and C only. The surface area of the skin sections was increased from 0.8 to 2.0 cm$^2$ and the applied dose was increased from 5 µL to 50 µL. The purpose of the study was to see if increased dose and surface area would increase penetration. Additionally, selected receptor solution samples were assayed by HPLC for cromoglycate content.

Due to low mass balance recover (<90%) a final limited pilot study on formulation A was conducted to further address the accountability of the applied dose. In this supplemental analysis, additional components of the cell and study system were evaluated for isotope content.

The results (where both radiolabeled and non-radiolabeled cromaglycate were measured), using 2.0 cm$^2$ chambers and a 50 µL dose for the percutaneous absorption of 3H-Cromoglycate from formulations A, B, and C are summarized in FIGS. 9 and 10, and Tables 18 and 19.

TABLE 18

Mean Flux (µg/cm$^2$/hr) Results: $^3$H-Cromoglycate Study #5 Summary; Analysis by HPLC
Percutaneous Absorption of $^3$H-Cromoglycate through Human Skin in vitro, over 24 hours, from a Single Dose Application (n = 1 Donors, with 1 replicate per formulation).

| Time (hr)* | A | B | C | Blank |
|---|---|---|---|---|
| 1 | 0.000 | 0.012 | 0.129 | 0.000 |
| 7 | 0.006 | 0.004 | 0.004 | 0.000 |

TABLE 18-continued

Mean Flux (µg/cm²/hr) Results: ³H-Cromoglycate
Study #5 Summary; Analysis by HPLC
Percutaneous Absorption of ³H-Cromoglycate through Human
Skin in vitro, over 24 hours, from a Single Dose Application
(n = 1 Donors, with 1 replicate per formulation).

| Time (hr)* | A | B | C | Blank |
|---|---|---|---|---|
| 18 | 0.002 | 0.000 | 0.000 | 0.000 |
| Total Pen (µg) | 0.177 | 0.130 | 0.590 | 0.000 |
| Total Pen (%) | 0.007 | 0.005 | 0.024 | 0.000 |

*Time as midpoint between samples.

This data is shown in FIG. 9.

TABLE 19

Mean Flux (µg/cm²/hr) Results: ³H-Cromoglycate
Summary
Analysis by Liquid Scintillation Counting
Percutaneous Absorption of ³H-Cromoglycate through Human
Skin in vitro, over 24 hours, from a Single Dose Application
(n = 1 Donors, with 1 replicate per formulation).

| Time (hr)* | A | B | C | Blank |
|---|---|---|---|---|
| 1 | 0.081 | 0.066 | 0.186 | 0.000 |
| 7 | 0.000 | 0.002 | 0.001 | 0.000 |
| 18 | 0.000 | 0.000 | 0.000 | 0.000 |
| Total Pen (µg) | 0.325 | 0.295 | 0.771 | 0.000 |
| Total Pen (%) | 0.013 | 0.012 | 0.031 | 0.000 |

*Time as midpoint between samples.

This data is shown in FIG. 10.

Example 9

Summary Results

The mass balance results from Examples 4-6 were averaged, and are shown in the tables below.

TABLE 20

Summary of Results: Formulations A, B and C
Percutaneous Absorption of ³H-Cromoglycate applied to
Human Skin in vitro over 8 hours from a Single Application.
Mean ± SE as Percent of Applied Dose

| Parameter | A | B | C |
|---|---|---|---|
| Receiver Compartment (%) | 0.096 ± 0.045 | 0.342 ± 0.196 | 0.739 ± 0.424 |
| Dermis (%) | 0.098 ± 0.055 | 0.252 ± 0.106 | 1.021 ± 0.442 |
| Epidermis (%) | 4.147 ± 1.393 | 6.452 ± 2.376 | 10.904 ± 6.981 |
| Surface Wash (%) | 38.640 ± 5.319 | 41.407 ± 5.052 | 45.317 ± 5.502 |
| Total Recovery (%) | 42.981 ± 6.258 | 48.454 ± 5.343 | 57.981 ± 11.698 |
| Number of Donors (n) | 4 | 4 | 5 |

TABLE 21

Summary of Results: Formulations D, E and F
Percutaneous Absorption of ³H-Cromoglycate applied to
Human Skin in vitro over 48 hours from a Single Application.
Mean ± SE as Percent of Applied Dose

| Parameter | D | E | F |
|---|---|---|---|
| Receiver Compartment (%) | 1.443 ± 1.364 | 0.015 ± 0.027 | 0.254 ± 0.190 |
| Dermis (%) | 0.324 ± .155 | 0.040 ± 0.012 | 1.066 ± 0.868 |
| Epidermis (%) | 1.680 ± 0.574 | 1.173 ± 0.761 | 20.866 ± 5.762 |
| Surface Wash (%) | 70.542 ± 21.84 | 43.869 ± 28.181 | 62.232 ± 22.398 |
| Total Recovery (%) | 73.989 ± 22.576 | 45.097 ± 28.924 | 84.417 ± 28.142 |
| Number of Donors (n) | 2 | 2 | 2 |

TABLE 22

Summary of Results: Formulations D2, E2 and F2
Percutaneous Absorption of ³H-Cromoglycate applied to
Human Skin in vitro over 48 hours from a Single Application.
Mean ± SE as Percent of Applied Dose

| Parameter | D2 | E2 | F2 |
|---|---|---|---|
| Receiver Compartment (%) | 0.663 ± 0.501 | 0.027 ± 0.024 | 0.660 ± 0.453 |
| Dermis (%) | 0.231 ± 0.062 | 0.123 ± 0.107 | 0.285 ± 0.202 |
| Epidermis (%) | 0.664 ± 0.169 | 1.892 ± 1.156 | 3.370 ± 2.763 |
| Surface Wash (%) | 69.364 ± 15.259 | 56.734 ± 20.174 | 71.055 ± 22.339 |
| Total Recovery (%) | 70.922 ± 15.575 | 58.776 ± 20.381 | 75.370 ± 19.620 |
| Number of Donors (n) | 3 | 3 | 3 |

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

The invention claimed is:
1. A topical administration composition comprising:
    (A) a cromolyn component selected from the group consisting of cromolyn and pharmaceutically acceptable salts thereof;
    (B) a delivery agent selected from the group consisting of N-(8-[2-hydroxybenzoyl]-amino)caprylic acid, 8-(2-hydroxybenzoylamino)-octanoic acid 2-{2-[2-(2-{2-[2-(2-methoxyethoxy)ethoxy]ethoxy}ethoxy)ethoxy]ethyoxy}ethyl ester, and pharmaceutically acceptable salts thereof;
    (C) a semi-aqueous vehicle which is unconjugated PEG/water; and
    (D) (a) an excipient,
        (b) a cream,
        (c) an ointment base,
        (d) a viscosity building agent,
        (e) a moisturizer,
        (f) a preservative,
        (g) a formulation vehicle, or
        (h) any combination thereof, wherein the topical administration composition provides a higher epidermal layer concentration of the cromolyn component over 8 hrs or 48 hrs after a single administration than a similar topical composition without the delivery agent compound.

2. The topical administration composition of claim 1, wherein the cromolyn component is disodium cromoglycate.

3. The topical administration composition of claim 1, wherein the delivery agent is monosodium N-(8-[2-hydroxybenzoyl]-amino)caprylate.

4. The topical administration composition of claim 1, wherein the delivery agent is 8-(2-hydroxybenzoylamino)-octanoic acid 2-{2-[2-(2-{2-[2-(2-methoxyethoxy)ethoxy]ethoxy}-ethoxy)ethoxy]-ethyoxy}ethyl ester.

5. The topical administration composition of claim 1, in the form of a cream, ointment, gel, suspension, or solution.

6. The topical administration composition of claim 1, further comprising an anti-allergic medication, a glucocorticoid, or a corticosteroid.

7. A method for administering an effective amount of a cromolyn component to a patient in need of thereof, comprising the step of topically administering the composition of claim 1.

8. A method of treating a skin condition in a patient in need thereof, comprising the step of topically administering to the patient an effective amount of the composition of claim 1.

9. The method of claim 8, wherein the skin condition is atopic dermatitis.

10. The topical pharmaceutical composition of claim 1, wherein the composition comprises from about 0.01 to about 7.0 percent by weight of the cromolyn component.

11. The topical pharmaceutical composition of claim 1, wherein the composition comprises from about 0.5 to about 4.0 percent by weight of the cromolyn component.

12. The topical pharmaceutical composition of claim 1, wherein the composition comprises about 3.0 percent by weight of the cromolyn component.

* * * * *